United States Patent
Panerai

(10) Patent No.: US 6,855,694 B2
(45) Date of Patent: Feb. 15, 2005

(54) METHOD OF TREATMENT OF AMYOTROPHIC LATERAL SCLEROSIS WITH A PROTEIN EXTRACTABLE FROM MAMMALIAN ORGANS

(75) Inventor: Alberto Panerai, Milan (IT)

(73) Assignee: Rakepoll Holding B.V., Amsterdam (NL)

( * ) Notice: Subject to any disclaimer, the term of this patent is extended or adjusted under 35 U.S.C. 154(b) by 85 days.

(21) Appl. No.: 10/297,671

(22) PCT Filed: Jun. 4, 2001

(86) PCT No.: PCT/EP01/06336
§ 371 (c)(1),
(2), (4) Date: Mar. 21, 2003

(87) PCT Pub. No.: WO01/93888
PCT Pub. Date: Dec. 13, 2001

(65) Prior Publication Data
US 2003/0162705 A1 Aug. 28, 2003

Related U.S. Application Data
(60) Provisional application No. 60/210,003, filed on Jun. 8, 2000.

(51) Int. Cl.$^7$ .............................................. A61K 38/00
(52) U.S. Cl. ..................... 514/12; 530/350; 424/185.1
(58) Field of Search .......................... 514/12; 530/350; 424/185.1

(56) References Cited

FOREIGN PATENT DOCUMENTS

| WO | 92 10197 A | 6/1992 |
|----|------------|--------|
| WO | 98 11909 A | 3/1998 |
| WO | 98 42366 A | 10/1998 |

OTHER PUBLICATIONS

Panerai et al; "Chronic Administration of UK–114, A Multifunctional Emerging Protein, Modulates the Th1/th2 Cytokine Pattern and Experimental Autoimmune Diseases"; Annals of the New York Academy of Sciences, Jun. 22, 1999, 876 229–35, XP000971426.

Primary Examiner—Karen Cochrane Carlson
Assistant Examiner—Anand U Desai
(74) Attorney, Agent, or Firm—Nixon & Vanderhye P.C.

(57) ABSTRACT

A method of treatment of patients affected by amyotrophic lateral sclerosis comprising the administration of an effective amount of a 14 kDa protein extractable from mammalian organs, particularly mammalian liver.

3 Claims, No Drawings

METHOD OF TREATMENT OF AMYOTROPHIC LATERAL SCLEROSIS WITH A PROTEIN EXTRACTABLE FROM MAMMALIAN ORGANS

This application claims the benefit of provisional application No. 60/210,003 filed Jun. 8, 2000.

The present invention concerns a method of treatment of patients affected by amyotrophic lateral sclerosis comprising the administration of an effective amount of a 14 kDa protein extractable from mammalian organs, particularly mammalian liver.

Amyotrophic lateral sclerosis (incidence of 1.4 to 4.7/100.000) also named motor neuron disease, is a degenerative disease characterized by progressive paralysis which affects elderly subjects (65–70 years), developing into complete paralysis and death and in a short time.

Several biochemical and genetic factors seem to be involved in the pathogenesis of ALS, which remains however to be still elucidated. An increase in some intracellular proteins (cytoskeleton) which affect cell activity and neurotransmission, seems to be the main cause of amyotrophic lateral sclerosis.

Although the aetiology of ALS is still largely unknown, according to a recent hypothesis, the first step in the onset of ALS appears to be connected with an increase of toxic factors such as oxygen radicals and the cited formation of protein cytoskeleton whereas the degenerative and progressive phase would seem to be at least partially activated and sustained by autoimmune mechanisms.

There is not specific treatment at present.

No experimental therapy proposed until now seemed particularly promising.

One of the major difficulties in developing an effective treatment for ALS is due to the lack of a reliable and predictive animal model so that the only definitive evidence on the actual effectiveness of a new therapy has to be obtained from clinical tests.

It has now been found that ALS can be effectively treated by administering to affected patients a 14 kDa protein which is normally present in mammalian liver, particularly in goat liver, and which can be prepared either by extraction or by recombinant DNA methods.

Said protein, hereinafter referred to with the abbreviation of MFP 14 (derived from Multiple Function Protein 14 kDa) has been disclosed by Ceciliani et al., FEBS Lett., 1996;393;147–50.

Its cytotoxic activity has been reported in Int.J.Oncol., 1996; 8:543–48 whereas its cDNA and expression in *E.coli* is reported by Colombo et al. in Biochem. Biophys. Acta, 1998;1442:49–59.

The preparation of the extractive protein as well as the preparation of the recombinant protein have been respectively disclosed in U.S. Pat. No. 5,792,744 and in PCT/EP/00 03003 which are herein incorporated by reference.

Therapeutic uses of this protein in the treatment of AIDS, autoimmune disease and TNF-induced disease have been disclosed in WO 98/42366.

Moreover, said protein has been found to be an inhibitor of protein synthesis, a modulator of cytokines synthesis as well as specific calpain activator.

MFP 14 has some sequence similarities with Heat shock proteins or HSP, with the protein binding to the Major Histocompatibilty Complex-1 (MHC-1 binding protein) and with the YER057C/YIL051C/Y5GF family of proteins having a still unknown function, highly evolutionary conserved from prokaryotes to mammals.

The invention, according to a first embodiment, provides therefore a method of treatment of ALS comprising the administration to patients in need of such treatment of a therapeutically active dose of MFP 14 or active fragment.

The invention also provides pharmaceutical compositions useful for treating amyotrophic lateral sclerosis containing as the active component an MFP 14 protein or active fragment.

The term MFP 14 refers also to proteins having high degree of homology with the amino acid sequence disclosed in the above-cited references. By high degree of homology, proteins having at least 70% homology with the 137 amino acid sequence of the native protein are meant. Preferably, the degree of homology is higher than 80%, more preferably higher than 90%.

The term "active fragment" refers to shorter sequences derived from the native or recombinant MFP 14 protein and still retaining the pharmacological activity of the parent sequence. It is in fact known that the therapeutic activity of a given protein does not always require a complete sequence, the activity being often confined to smaller regions, e.g. to N-terminal, Carboxy-terminal or internal regions. In such an event, it may be advantageous the administration of the active fragment rather than the intact protein in view of lower production costs, higher metabolic stability and other possible advantages connected with the administration of polypeptides having lower molecular weight.

The fragments and homologues of MFP 14 may also derive from deletion, substitutions and/or insertion mutation of amino acids. For instance, it is known that the so called "conservative" mutations, i.e. the substitution of an amino acid with another one of the same category (acidic, basic, neutral, hydrophilic or lipophilic), is usually acceptable for the preservation of activity.

The use of recombinant MFP 14 is particularly preferred in view of the easier availability and standardization of production methods.

Alternatively, an extract comprising MFP 14 such as that disclosed in WO 92/10197 may also be used.

For the considered therapeutic use, MFP 14 or active fragments thereof will be administered parenterally, e.g. by intramuscular or subcutaneous route, in form of sterile solutions or suspensions in acceptable carriers such as saline solutions, oils for parenteral administration and the like.

Other administration routes can also be envisaged, for instance the oral or transdermal route, using known methods for the delivery of proteins or polypeptides by these routes (e.g. by means of liposomes or micro-encapsulation methods).

The administration of MFP 14 proteins could also be carried out using gene therapy protocols, for instance by administering suitable vectors, which may deliver to target cells a gene sequence coding for MFP 14. Suitable vectors as well as corresponding control sequences and protocols are disclosed in FASEB J. 9, 190–199, 1995 and in Nature 392 (suppl. 30 April ) 25–30, 1998.

MFP 14 dose range which was found to be effective in the treatment of ALS is comprised from about 1 mg to 10 mg/day.

The dose can be divided in more than one daily administration, for instance two or three administrations. In particular cases, the administrations can also be separated one from the other by longer period of times, up to 1–4 weeks. This can particularly apply to the chronic long-term treatment, once the first cycle of treatment has been completed.

The dosage regimen can anyhow vary within wide limits, in view of the very low toxicity of MFP 14, so that the skilled physicians will easily adapt the doses according to individual patients' requirements, particularly taking into consideration the age, sex, weight of the patient and the seriousness and advancement stage of the disease.

It has also been found that the administration of ubiquitin in combination with MFP 14 is advantageous in the treatment of ALS. Ubiquitins belong to a well-known family of proteins, the use of which has been proposed for several pathologies, which do not have anything in common with ALS. For the considered therapeutic use, ubiquitins will be administered, preferably contemporaneously, together with MFP 14, at a dosage ranging from about 1 mg to 10 mg/day.

According to a further embodiment, the invention provides therefore also pharmaceutical compositions comprising as the active ingredient a combination of MFP 14 and of ubiquitin, in admixture with a suitable pharmaceutical carrier.

The administration of MFP 14 or of fragments thereof, optionally in combination with ubiquitin, proved to be effective in clinical trials carried out on patients with ALS at different stages. In particular the treatment of the invention turned out to be effective both in the first stages as well as in the late stages of this pathology, inducing a significant recovery of the motion function and an improvement of the social life in affected patients.

The following examples are given to further illustrate the invention in more detail.

EXAMPLE 1

Pharmaceutical Composition of MFP 14 in Form of Vials for Parenteral Administration

| | |
|---|---|
| Lyophilised Recombinant MFP 14 obtained according to PCT/EP/00 03003 | mg 0.5 |
| Sterile Saline Solution | ml 2 |

EXAMPLE 2

Pharmaceutical Composition of MFP14 and Ubiquitin in Form of Vials for Parenteral Administration

| | |
|---|---|
| Lyophilised Recombinant MFP 14 obtained according to PCT/EP/00 03003 | mg 0.5 |
| Ubiquitin | mg 1 |
| Sterile Saline Solution | ml 2 |

EXAMPLE 3

Clinical Tests

Four patients suffering from amyotrophic lateral sclerosis for 2/4 years were treated.

In three patients, the first and second motor neurons were affected, with marked atrophy at the distal extremities of the upper limbs and spasticity of the lower limbs. In the fourth patient, also dementia was present (ALS plus dementia). In all patients, phonation and deglutition were remarkably impaired, the fourth patient was fed through nasal-gastric probe.

After about 15 days in the first three patients and already after 7 days in the patient with dementia-ALS a marked improvement of deglutition and phonation was observed. Limb symptoms remained steady in three patients; in one patient an improvement in strength and deambulation was observed.

After one-month treatment, the results remained steady and the worsening typical of the disease was not observed even after several weeks.

What is claimed is:

1. A method of treatment of patients affected by amyotrophic lateral sclerosis comprising the administration to patients in need of such treatment of a therapeutically active dose of multiple function protein 14 kDa.

2. A method according to claim 1 wherein multiple function protein 14 kDa is selected from recombinant multiple function protein 14 kDa or multiple function protein 14 kDa extracted from goat liver.

3. A method according to claim 1 further comprising the administration of ubiquitin.

* * * * *